US011228567B2

(12) United States Patent
Armitage et al.

(10) Patent No.: US 11,228,567 B2
(45) Date of Patent: *Jan. 18, 2022

(54) SYSTEM AND METHOD FOR RECEIVER TO ANONYMOUS DONOR COMMUNICATION

(71) Applicant: Oklahoma Blood Institute, Oklahoma City, OK (US)

(72) Inventors: John Brooks Armitage, Oklahoma City, OK (US); Justin Ryan Redwine, Oklahoma City, OK (US)

(73) Assignee: Oklahoma Blood Institute, Oklahoma City, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/437,247

(22) Filed: Feb. 20, 2017

(65) Prior Publication Data

US 2018/0115527 A1 Apr. 26, 2018

Related U.S. Application Data

(63) Continuation of application No. 15/299,094, filed on Oct. 20, 2016, now Pat. No. 11,038,848.

(51) Int. Cl.
*H04L 29/06* (2006.01)
*G06F 21/62* (2013.01)
(Continued)

(52) U.S. Cl.
CPC ...... *H04L 63/0421* (2013.01); *G06F 21/6254* (2013.01); *G06F 21/6263* (2013.01);
(Continued)

(58) Field of Classification Search
CPC . H04L 63/0421; H04L 63/083; H04L 63/126; H04L 9/3236; H04L 9/3242;
(Continued)

(56) References Cited

U.S. PATENT DOCUMENTS

| 9,262,623 | B2 * | 2/2016 | Stecher | G06F 21/45 |
| 2003/0040835 | A1 * | 2/2003 | Ng | G16H 10/40 |
| | | | | 700/214 |

(Continued)

FOREIGN PATENT DOCUMENTS

EP 1185069 3/2002

OTHER PUBLICATIONS

L. Xi, "Secure Anonymous Donation Protocol," 2009 WRI World Congress on Computer Science and Information Engineering, 2009, pp. 106-110, doi: 10.1109/CSIE.2009.145. (Year: 2009).*

(Continued)

*Primary Examiner* — Saleh Najjar
*Assistant Examiner* — Khalid M Almaghayreh
(74) *Attorney, Agent, or Firm* — Dunlap Codding, P.C.

(57) ABSTRACT

An automated system comprising a processor and a database are described. The processor executes communication software reading: at least one image corresponding to an identifier of a blood product from a donor; and at least one database storing at least one communication from a receiver of the blood product. The communication software executed by the processor determines an intermediary from the identifier and contacts the intermediary to obtain contact information of the donor.

16 Claims, 18 Drawing Sheets

(51) Int. Cl.
*H04W 12/02* (2009.01)
*G16H 10/60* (2018.01)
*G16H 40/20* (2018.01)
*G06K 7/10* (2006.01)
*G06K 7/14* (2006.01)

(52) U.S. Cl.
CPC ....... *G06K 7/10861* (2013.01); *G06K 7/1413* (2013.01); *G16H 10/60* (2018.01); *G16H 40/20* (2018.01); *H04W 12/02* (2013.01); *G06F 2221/2115* (2013.01); *H04L 63/083* (2013.01)

(58) Field of Classification Search
CPC . H04L 2209/38; H04L 2209/59; G06F 19/00; G06F 19/3418; G06F 21/6254; G06F 21/6263; G06F 2221/2115; G06Q 30/0279; G06Q 20/108; G06Q 20/389; G16H 40/20; G06K 7/10861; G06K 7/1413
USPC .......... 726/28, 3; 705/74, 53, 64, 78, 3, 325, 705/333
See application file for complete search history.

(56) References Cited

U.S. PATENT DOCUMENTS

| | | | | |
|---|---|---|---|---|
| 2003/0069480 | A1* | 4/2003 | Ng | A61B 5/150786 600/300 |
| 2004/0102683 | A1* | 5/2004 | Khanuja | H04L 67/2838 600/300 |
| 2004/0111281 | A1* | 6/2004 | Witter | G06Q 30/0601 705/26.1 |
| 2005/0055379 | A1* | 3/2005 | Yamazaki | G06Q 10/10 |
| 2006/0271406 | A1* | 11/2006 | Califano | G16H 10/40 705/3 |
| 2007/0219826 | A1* | 9/2007 | Brodsky | A61M 1/387 705/2 |
| 2008/0033744 | A1* | 2/2008 | Jones | G06Q 30/02 705/329 |
| 2009/0089099 | A1* | 4/2009 | Kranz | A61B 90/96 705/3 |
| 2010/0049542 | A1* | 2/2010 | Benjamin | G16H 40/20 705/2 |
| 2012/0038651 | A1* | 2/2012 | Case | G06Q 10/087 345/440 |
| 2012/0109677 | A1* | 5/2012 | Hillyer | G01N 33/80 705/2 |
| 2012/0265099 | A1* | 10/2012 | Goodnow, II | G16H 10/40 600/573 |
| 2013/0060574 | A1* | 3/2013 | Perlman | G16H 10/60 705/2 |
| 2013/0151432 | A1* | 6/2013 | Kashner | G06Q 40/02 705/329 |
| 2014/0259724 | A1* | 9/2014 | McCarthy | F26B 5/06 34/284 |
| 2015/0113605 | A1* | 4/2015 | Henderson | G06Q 50/01 726/4 |
| 2015/0281183 | A1* | 10/2015 | Postrel | H04L 51/28 709/206 |
| 2016/0036739 | A1* | 2/2016 | Glass | H04W 4/12 709/206 |
| 2016/0277435 | A1* | 9/2016 | Salajegheh | H04L 63/1416 |
| 2017/0330249 | A1* | 11/2017 | Celise | G06F 16/2379 |

OTHER PUBLICATIONS

PCT International Search Report and Written Opinion regarding PCT App. No. PCT/US2017/43440 dated Oct. 12, 2017.
Office Action regarding U.S Patent Application No. 15/299,094, dated Aug. 3, 2018.
USPTO Office Action regarding U.S. Appl. No. 15/299,094, dated Mar. 6, 2019.
USPTO Office Action regarding the U.S. Appl. No. 15/437,247, dated Sep. 6, 2019.
Extended European Search Report regarding European Patent App. No. 17862411.0 dated Apr. 7, 2020.
Office Action regarding U.S Appl. No. 15/299,094, dated Sep. 29, 2020.
Correspondence from George C. Beck to Marc A. Brockhaus regarding Message My Donor dated Sep. 3, 2021.
"Be the Match", [online] https://web.archive.org/web/20131109063950/https://bethematch.org/transplant-basics/do-patients-and-donors-meet/, Nov. 9, 2013, 22 pages.
"Be the Match", [online] https://web.archive.org/web/20140609051128/https://bethematch.org/For-Patients-and-Families/Finding-a-donor/Contact-with-your-donor/, Jun. 9, 2014, 4 pages.
European Examination Report (EP 17862411.0), dated Oct. 21, 2021; 7 pgs.

* cited by examiner

SYSTEM AND METHOD FOR RECEIVER TO ANONYMOUS DONOR COMMUNICATION

INCORPORATION BY REFERENCE

The present invention claims priority to and incorporates by reference the entirety of the patent application identified by U.S. Ser. No. 15/299,094, filed on Oct. 20, 2016.

BACKGROUND

In the information age, providers of products in certain situations would like to remain anonymous to the final receiver. In some cases, receivers of the product would still like to communicate with the provider while protecting the provider's anonymity. For example, within the blood donor industry, a donor of blood or blood products generally remains anonymous from the recipient of the blood or blood product. The recipient, however, may have a need to thank the donor without compromising the anonymity of the blood donor process.

Additionally, given the possibility of messages being sent from a recipient to a blood donor being sensitive in nature, human approval during communication between receivers and providers may be needed prior to delivery of the communication.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts, and further wherein.

DETAILED DESCRIPTION OF EXEMPLARY EMBODIMENTS

Figure 1:
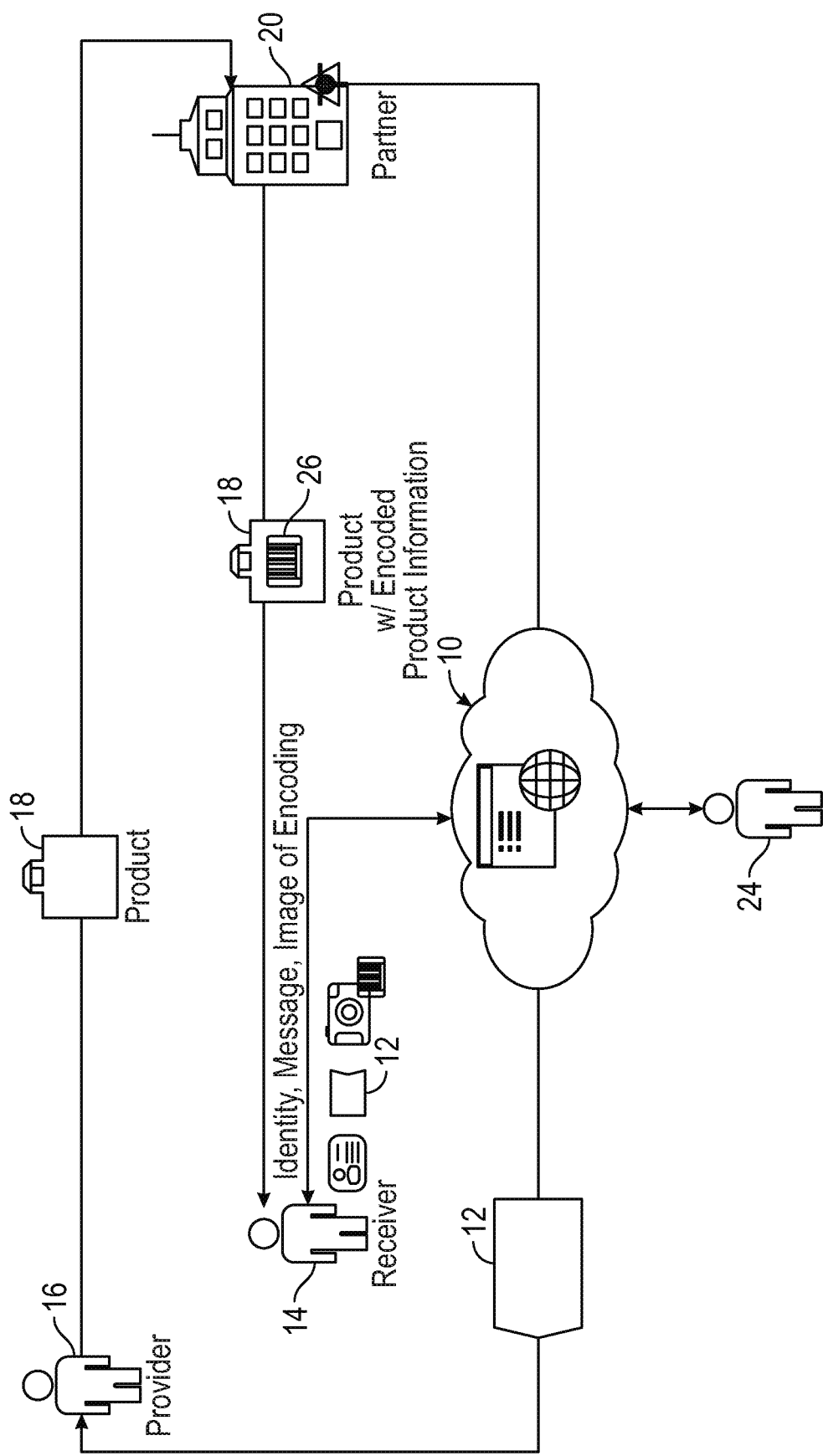
FIG. 1 illustrates a block diagram of an exemplary communication system in accordance with the present disclosure, configured to provide one or more communications between one or more receivers and one or more anonymous providers of an accommodation.

Generally, providers of certain products would like to remain anonymous to a final receiver. In some cases, the final receiver of the product would like to communicate with the provider while still protecting the provider's anonymity. Given the possibility of communication being sensitive in nature, human approval during such communication may be needed prior to delivery of the communication The present disclosure, in at least certain embodiments, is directed to systems and methods to allow providers of an accommodation, such as a product or a service, to provide a method for a receiver of the accommodation to communicate with the anonymous provider of the accommodation. An accommodation is anything that fulfills a need or want of the receiver, such as bodily tissue (e.g., blood or organ(s)), entertainment (e.g., a play, a movie, a park), lodging, food, medication, healthcare, advice and/or assistance, or the like. The receiver may have the ability to create and/or send the communication to the provider via an online-interface with a back-end receiver look-up application program interface (API), for example. Additionally, an administrator review process may be included for review of the communication prior to delivery to the anonymous provider.

In some embodiments, a repository of communications provided by the receiver may be collected and/or stored. One or more Internet servers may provide one or more graphical user interfaces (GUI), for example, for creation of one or more communications by a receiver of an accommodation from a provider. Additionally, one or more images of one or more identifying characteristics of the accommodation (e.g., encoded product information) from the provider, may be collected. In some embodiments, an administrator review process may also be used to review one or more submitted communications, communicate information regarding such communication(s) (e.g., forward approved communications to the provider), and/or archive communications (e.g., approved communications, denied communication). In some embodiments, provider information (e.g., first name, last name, e-mail, unique identifier) may be retrieved and/or requested, for example, via one or more API.

Before explaining at least one embodiment of the presently disclosed and claimed inventive concepts in detail, it is to be understood that the presently disclosed and claimed inventive concepts are not limited in their application to the details of construction, experiments, exemplary data, and/or the arrangement of the components set forth in the following description or illustrated in the drawings. The presently disclosed and claimed inventive concepts are capable of other embodiments or of being practiced or carried out in various ways. Also, it is to be understood that the phraseology and terminology employed herein is for purpose of description and should not be regarded as limiting.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, certain well-known features may not be described in detail in order to avoid unnecessarily complicating the instant disclosure.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

The term "and combinations thereof" as used herein refers to all permutations or combinations of the listed items preceding the term. For example, "A, B, C, and combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. A person of ordinary skill in the art will understand that typically there is no limit on the number of items or terms in any combination, unless otherwise apparent from the context.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The use of the terms "at least one" and "one or more" will be understood to include one as well as any quantity more than one, including but not limited to each of, 2, 3, 4, 5, 10, 15, 20, 30, 40, 50, 100, and all integers and fractions, if applicable, therebetween. The terms "at least one" and "one or more" may extend up to 100 or 1000 or more, depending on the term to which it is attached; in addition, the quantities of 100/1000 are not to be considered limiting, as higher limits may also produce satisfactory results.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein qualifiers such as "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, and combinations thereof, for example.

Software may include one or more computer readable instructions that when executed by one or more components cause the component to perform a specified function. It should be understood that algorithms or process instructions described herein may be stored on one or more non-transitory computer readable medium. Exemplary non-transitory computer readable medium may include random access memory, read only memory, flash memory, and/or the like. Such non-transitory computer readable mediums may be electrically based, optically based, and/or the like.

Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), field programmable gate array (FPGA), a combination of hardware and software, and/or the like. The term "processor" as used herein means a single processor or multiple processors working independently or together to collectively perform a task.

Additionally, it is to further be understood that the provider and receiver as described herein are not limited to human beings, and may comprise, an animal, a thing, a computer, a server, a website, a business entity, a human, a group of humans, a virtual computer, combinations thereof, and the like, for example.

Certain exemplary embodiments of the invention will now be described with reference to the drawings. In general, such embodiments relate to communication between a receiver and an anonymous provider of an accommodation.

Referring to the Figures, and in particular FIG. 1, shown therein is a block diagram of an exemplary communication system 10 configured to provide one or more communications 12 between one or more receivers 14 and one or more anonymous providers 16 of an accommodation, which is depicted by way of example in FIG. 1, as product 18. Communications 12 may be verbal communications, written communications, and/or non-verbal communications. Additionally, communications 12 may be provided via text, video, audio, and/or the like. For example, the communication 12 may be a video of the receiver 14 of the accommodation saying "Thank you". In another example, the communication 12 may be a text message from the receiver 14 of the product 18 describing alterations in their health, death, or even inappropriate comments.

In some embodiments, one or more intermediaries 20 may be configured to provide a review process for the one or more communications 12 via one or more administrators 24 prior to receipt by the one or more providers 16 of the accommodation, such as the product 18.

For simplicity in description, the following disclosure uses the exemplary communication system 10 in relation to blood product donors. However, as one skilled in the art will recognize, the communication system 10 may relate to any method wherein communications 12 may be intended between the receiver 14 and the anonymous provider 16 of the accommodation. For example, in charitable giving, identity of donors providing gifts to recipients may be kept anonymous (e.g., Salvation Army Angel Tree). The gifts may be made to third parties, such as municipalities or charitable organizations who provide the accommodation to the receiver(s) 14. For example the anonymous provider 16 may make a cash donation to a charitable organization who funds and/or takes care of a park for receiver(s) 14. Receiver (s) 14 may want to provide a communication 12 for the gift to the anonymous donor(s) (i.e., providers 16).

Referring again to FIG. 1, in the communication system 10 as it relates to blood product donors, the provider 16 may be the donor of blood product 18. Generally, blood collection centers may keep personal health information when blood product 18 is donated. Such information may include identification information, safeguards for blood supply, testing and follow-up activities of the blood, matching information for blood product and recipients, and other donation-related activities that may be necessary for medical purposed or required by law. However, identifying characteristics of providers 16 of the blood products 18 (e.g., e-mail, home address, name) may be kept confidential (e.g., from receivers 14 and/or other entities). In some embodiments, the blood collection center may be the intermediary 20. In some embodiments, the intermediary 20 may serve as an aggregate for several blood collection centers.

The provider 16 may donate and/or give the product 18. The terms blood product 18 and product 18 may be used interchangeably herein to describe an exemplary use for the system 10. The product 18 may be any blood product capable of being donated and/or given, such as, for example, white blood cells, red blood cells, plasma, and/or all other forms or formations of blood and/or plasma. In another example, the product 18 may be organ, tissue material, or other donated items.

The product 18 may include one or more identifiers 26 having one or more identifying characteristics configured to track and/or identify the product 18. The identifier 26 may be attached, fastened to or otherwise associated with the product 18 for delivery from the intermediary 20 to the receiver 14. For example, when the accommodation is a park, a movie or the like, the identifier 26 may be attached to a sign located on or near the park, or on a ticket or other item associated with the movie. Each identifier 26 may be individualized to each product 18. The identifier 26 may include, but is not limited to, a bar code, near field communication (NFC) tag, radio frequency identification (RFID) tag, quick response (QR) code, a numeric code, an alphabetical code, an alphanumeric code and/or the like. For example, blood products 18 may be labelled using the ISBT 128 donation identification number (DIN), the global standard for identification of medical products of human origin (e.g., blood, cells, tissue, and the like). The donation identification number may be thirteen characters long, for example, and provide identifying characteristics composed of three parts: (1) Facility Identification Number (FIN)—a 5 character identification number assigned to a blood collection center (e.g., the intermediary 20); (2) a 2 digit number indicating the year in which the DIN was assigned; and (3) a 6-digit sequence number controlled and maintained by the blood collection center (e.g., the intermediary 20). The sequence number controlled by the blood collection center (e.g., the intermediary 20) may include identifying characteristics of the product 18 including, but not limited to, blood screeners, phlebotomists, shipping preferences, and/or the like. The identifying characteristics, however, do not provide direct contact information for the provider 16 (e.g., e-mail, home address, and name).

Generally, once the blood product 18 is collected from the provider 16, and the identifier 26 is fastened or attached to the blood product 18, the blood product 18 may be transferred to the receiver 14. The receiver 14 is generally a person, animal or thing in receipt of the product 18. For example, the receiver 14 may be a person receiving the blood product 18 (e.g., via a blood transfusion). Alternatively, the receiver 14 may be a person associated with the person, animal or thing in receipt of the blood product 18 (e.g., a friend or family member).

Figure 2:
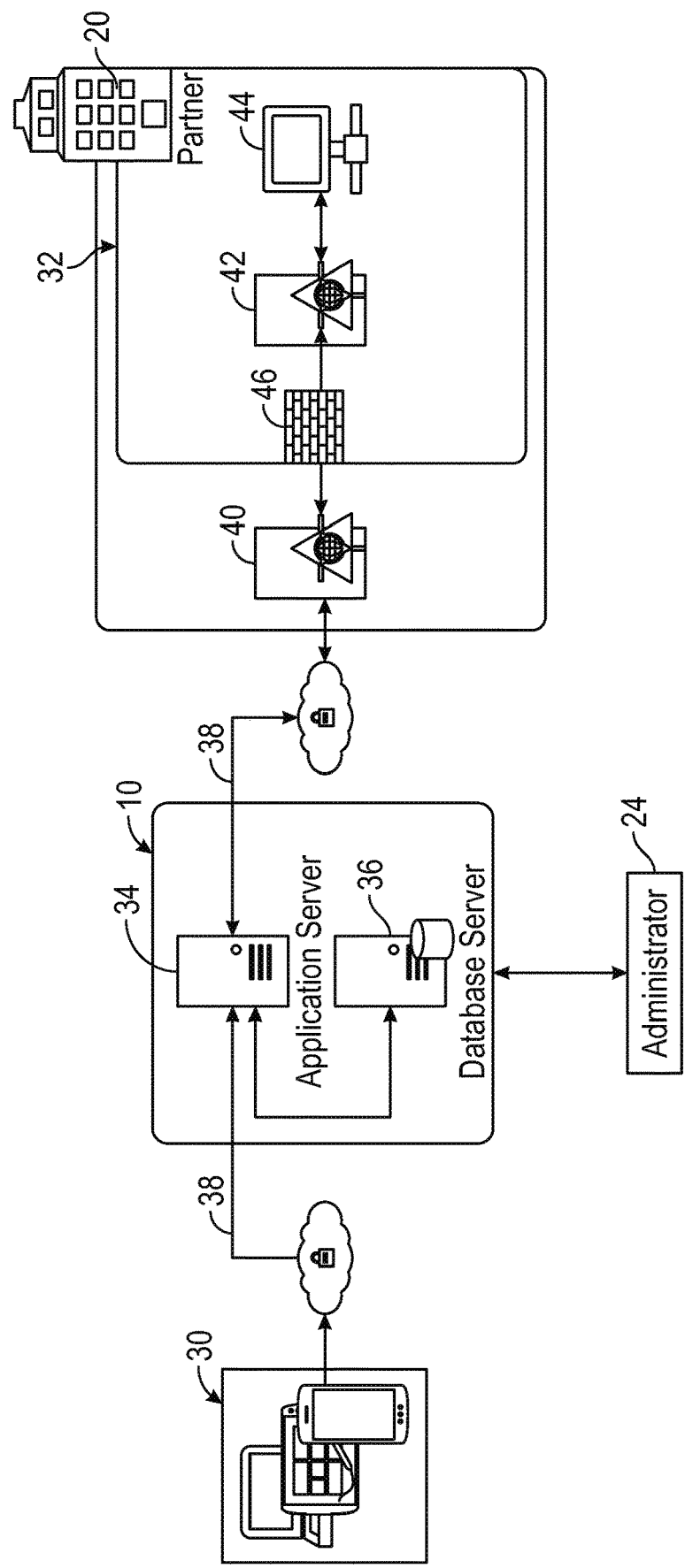
FIG. 2 illustrates a block diagram of hardware for the exemplary communication system configured to provide communications from an exemplary receiver system to an exemplary intermediary system.

Referring to FIGS. 1 and 2, the receiver 14 may desire to send one or more communications 12 to the provider 16 regarding the product 18. In some embodiments, the receiver 14 may only send one or more communications 12 to the provider 16 regarding the product 18, without having any indication of their identity (including an anonymous name, a name of an avatar associated with the receiver 14 or the like) being disclosed to the provider 16, or contracting with the provider 16 for the physical shipment of any item(s) or the provision of services. Contact information for the provider 16, however, is to remain confidential to the receiver 14, at least, and may remain confidential to other entities outside of the intermediary 20 and/or affiliates of the intermediary 20.

Generally, the receiver 14 contacts the communication system 10 and provides the one or more communications 12 to the communication system 10. The communication system 10 may then analyze the identifier 26 to determine the intermediary 20, or affiliate of the intermediary, the provider 16 who may have donated or given blood product 18. The identifier 26, however, may not provide contact information of the provider 16, or any financial information including amounts of money, credit card information, bank account information, bank routing numbers or the like. The communication system 10 may communicate the communication 12 to the intermediary 20 to determine contact information for the provider 16. In some embodiments, the communication system 10 may coordinate transfer of the one or more communications 12 from the receiver 14 to the intermediary 20. The intermediary 20, having the contact information of the provider 16, may then provide the one or more communications 12 to the provider 16. In some embodiments, the intermediary 20 may provide contact information of the provider 16 to the communication system 10. The communication system, having contact information of the provider 16 may then coordinate transfer of the one or more communications 12 from the receiver 14 to the provider 16. In some embodiments, the intermediary 20 only facilitates providing the one or more communications 12 from the receiver 14 to the provider 16. In some embodiments, the intermediary 20 does not provide financial or payment services between the receiver 14 and the provider 16. In some embodiments, the intermediary 20 neither facilitates the contracting nor the delivery of one or more physical items or services from the provider 16 to the receiver 14.

Referring to FIG. 2, the receiver 14 may use one or more receiver systems 30 to communicate the one or more communications 12 to the communication system 10. The one or more receiver systems 30 may include one or more processors. In some embodiments, the one or more processors may be partially or completely network-based or cloud-based. The one or more processors may or may not be located in a single physical location. Additionally, multiple processors may or may not be located in a single physical location.

In some embodiments, the receiver system 30 may include one or more image capturing devices capable of receiving information from a user and/or processor, and transmitting such information to the communication system 10. The one or more image capturing input devices may include, but are not limited to, a cellular phone camera, The communication system 10 may be a system or systems that are able to embody and/or execute the logic of the processes described herein. Logic embodied in the form of software instructions and/or firmware may be executed on appropriate hardware. For example, logic embodied in the form of software instructions or firmware may be executed on a dedicated system or systems, a distributed processing system, and/or the like. In some embodiments, logic may be implemented in a stand-alone environment operating on a single computer system and/or logic may be implemented in a networked environment, such as a distributed system using multiple computers and/or processors. For example, a subsystem of the communication system 10 may be located within at and/or within the intermediary 20, and another subsystem of the communication system 10 may be located in a data center having multiple computers, servers, and/or processors networked together.

In some embodiments, the communication system 10 may include one or more processors configured to communicate with the receiver system 30 and an intermediary system 32 enabling the transfer of the one or more communications 12 from the receiver system 30 to the intermediary system 32 for delivery to the provider 16. The communication system 10 as shown in FIG. 2 has an application server 34 and a database server 36. It should be noted that a single server or additional servers may be included. In some embodiments, one or both of the application server 34 and/or the database server 36 may be network-based, cloud-based, and variations thereof. As used herein, the terms "network-based", "cloud based", and any variations thereof, may include the provision of configurable computational resources on demand via interfacing with a computer and/or computer network, with software and/or data at least partially located on the computer and/or computer network, by pooling processing power of two or more networked processors.

The communication system 10 may be capable of interfacing and/or communicating with the receiver system 30 and/or the intermediary system 32 via a network 38. Additionally, the application server 34 and the database server 36 may be capable of communicating with each other via the network 38.

The network 38 may be almost any type of network. For example, the network 38 may interface by optical and/or electronic interfaces, and/or may use a plurality of network topographies and/or protocols including, but not limited to, Ethernet, TCP/IP, circuit switched paths, and/or combinations thereof. For example, in some embodiments, the network 38 may be implemented as the World Wide Web (or Internet), a local area network (LAN), a wide area network (WAN), a metropolitan network, a wireless network, a cellular network, a Global System for Mobile Communications (GSM) network, a code division multiple access (CDMA) network, a 3G network, a 4G network, a satellite network, a radio network, an optical network, a cable network, a public switched telephone network, an Ethernet network, combinations thereof, and/or the like. Additionally, the network 38 may use a variety of network protocols to permit bi-directional interface and/or communication of data and/or information. It is conceivable that in the near future, embodiments of the present disclosure may use more advanced networking topologies.

In some embodiments, the network 38 may be the Internet and/or other network. For example, if the network 38 is the Internet, a primary user interface of the donor communication delivery software may be delivered through a series of web pages. It should be noted that the primary user interface of the donor communication delivery software may be replaced by another type of interface, such as, for example, a Windows-based application.

The application server 34 and the database server 36 may be capable of reading and/or executing processor executable code and/or capable of creating, manipulating, retrieving, altering and/or storing data structures into one or more memories. The one or more memories may be capable of storing processor executable code. Additionally, the one or more memories may be implemented as a conventional non-transitory memory, such as, for example, random access memory (RAM), a CD-ROM, a hard drive, a solid state drive, a flash drive, a memory card, a DVD-ROM, a floppy disk, an optical drive, combinations thereof, and/or the like, for example.

In some embodiments, the one or more memories may be located in the same physical location. Alternatively, one or more memories may be located in a different location as the communication system 10 and communicating via a network, such as the network 38. Additionally, one or more of the memories may be implemented as a "cloud memory" (i.e., one or more memories may be partially or completely based on or accessed using a network, such as network 38, for example).

The one or more memories may store processor executable code and/or information comprising one or more databases and program logic. In some embodiments, the processor executable code may be stored as a data structure, such as a part of database and/or data table, for example. In some embodiments, one of the databases may be an identifier database storing identifying characteristics analyzed and determined from the identifier 26 of the product 18. In some embodiments, one of the databases may be a communication database storing one or more communications 12 received from the receiver system 30. In some embodiments, one of the databases may be an image database storing images of one or more identifiers 26. In some embodiments, one of the databases may be an archive communication database, storing one or more archived communications 12. In some embodiments, one of the databases may be a rejected communication database, storing one or more rejected communications 12. In some embodiments, one of the databases may be a receiver database, storing one or more characteristics of receivers 14.

Generally, program logic of the communication system 10 may decode one or more identifiers 26 associated with the product 18 to identify one or more intermediaries 20. For example, using the 13-digit code from the identifier 26, the communication system 10 may extract the first 5 digits to determine the intermediary 20. Through identification of the one or more intermediaries 20, the communication system 10 may contact the intermediary 20 and, in some embodiments, query the intermediary 20 for information regarding the provider 16 by using the remaining 8 digits of the identifier 26. The intermediary 20 may use the identifier 26 to determine further information related the provider 16, including contact information. In some embodiments, the intermediary 20 may transmit the additional information to the communication system 10. In some embodiments, the administrator 24 associated with the intermediary 20 may have access to the communication system 10 for review of the one or more communications 12 prior to transmission of the communications 12 to the provider 16.

In some embodiments, the communication system 10 may communicate with the intermediary system 32 via a representational state transfer (Restful Service) API 40. To that end, the Restful Service API may communicate with the intermediary system 32. The intermediary system 32, in some embodiments, may include an intermediary API 42 for communicating with one or more processors 44 of the intermediary system 32. In some embodiments, a firewall 46 may exist between the Restful Service API 40 and the intermediary system 32. In some embodiments, the intermediary system 32 may be safeguarded behind the firewall 46. It should be noted that the communication system 10 may communicate with the intermediary system 32 via other methods including, but not limited to, simple object access protocol (SOAP), direct communication, and/or the like.

The intermediary system 32 may include one or more processors 44 and/or computer systems. In some embodiments, the one or more processors 44 and/or computer systems may be partially or completely network-based or cloud-based. The one or more processors 44 and/or computer systems may or may not be located in a single physical location. Additionally, multiple processors may or may not be located in a single physical location.

In some embodiments, the administrator 24 may be associated with the intermediary 20. As such, the administrator 24 may use one or more processors associated with the intermediary 20 to communicate with the communication system 10 for administrative review of the one or more communications 12 as discussed in further detail herein. In some embodiments, the administrator 24 may use the communication system 10 for administrative review of the one or more communications 12. Alternatively, the administrator 24 may use a third party processor to communicate with the communication system 10 for administrative review of the one or more communications 12.

Figure 3:
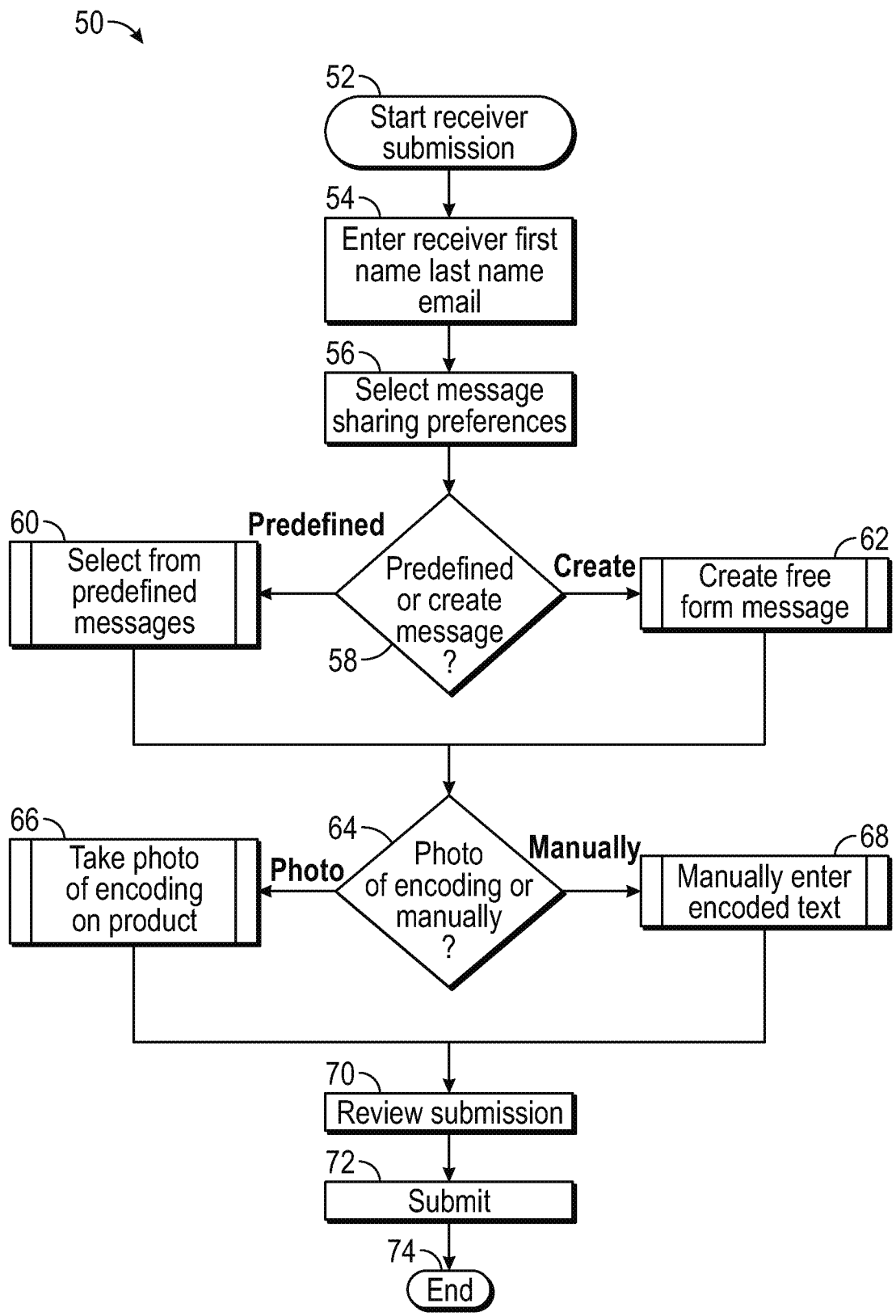
FIG. 3 illustrates a flow chart of an exemplary method for submittal of one or more communications by a receiver using the communication system illustrated in FIGS. 1 and 2.

FIG. 3 illustrates a flow chart 50 of an exemplary method for submittal of the one or more communications 12 by the receiver 14 to the communication system 10. FIGS. 4-13 illustrate exemplary screen shots of the method described in relation to FIG. 3.

Figure 4:
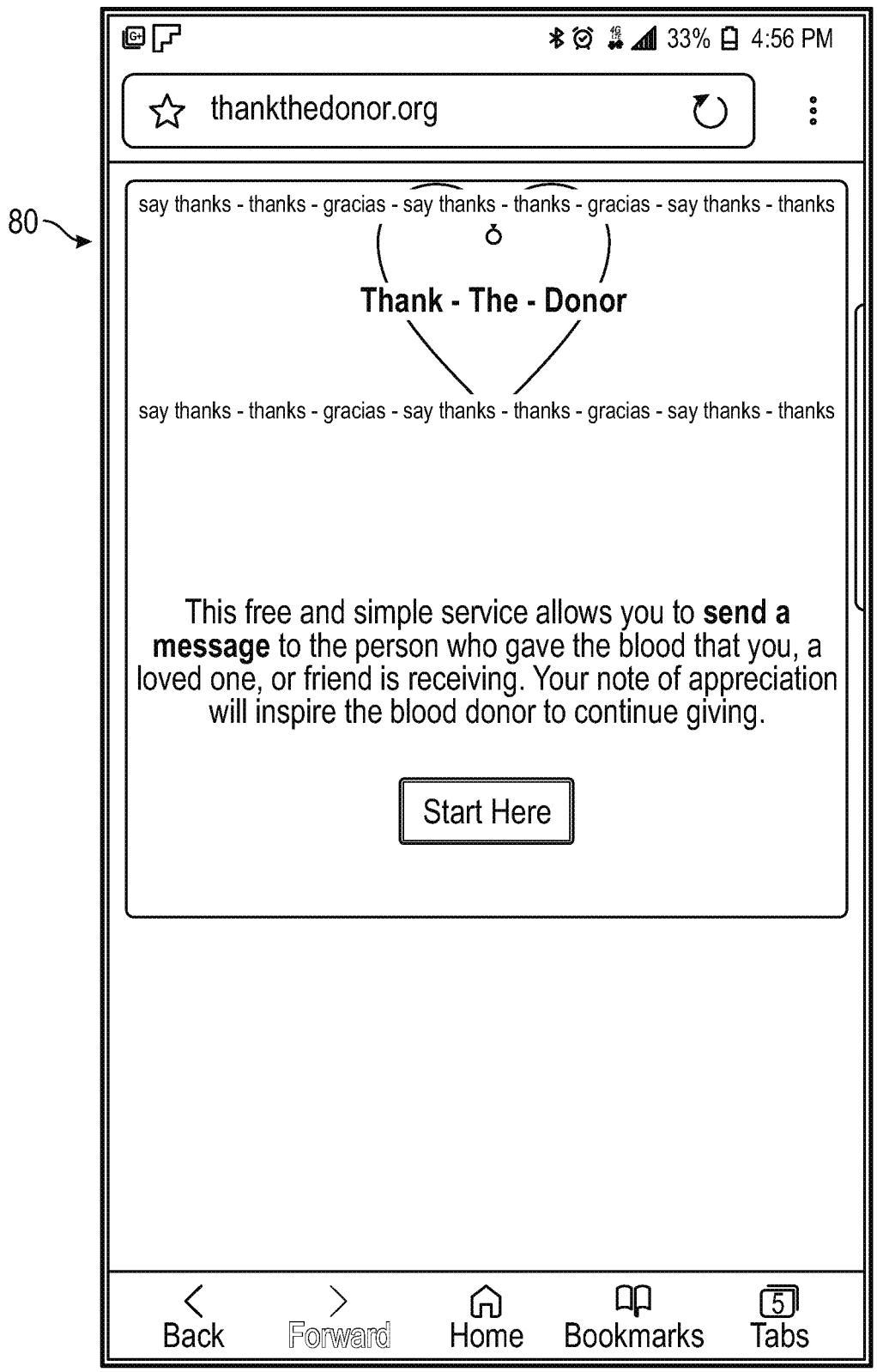
FIGS. 4-13 illustrate exemplary screen shots of the exemplary method for submittal of one or more communications described in relation to FIG. 3.

Referring to FIGS. 3 and 4, in a step 52, the process of submission may begin by the receiver 14 accessing the communication system 10. In some embodiments, the communication system 10 may provide one or more network servers with one or more graphical user interfaces (GUI), for example, for creation of one or more communications 12 at the receiver system 30. A screenshot 80 on FIG. 4 illustrates an exemplary landing page for entry.

Figure 5:
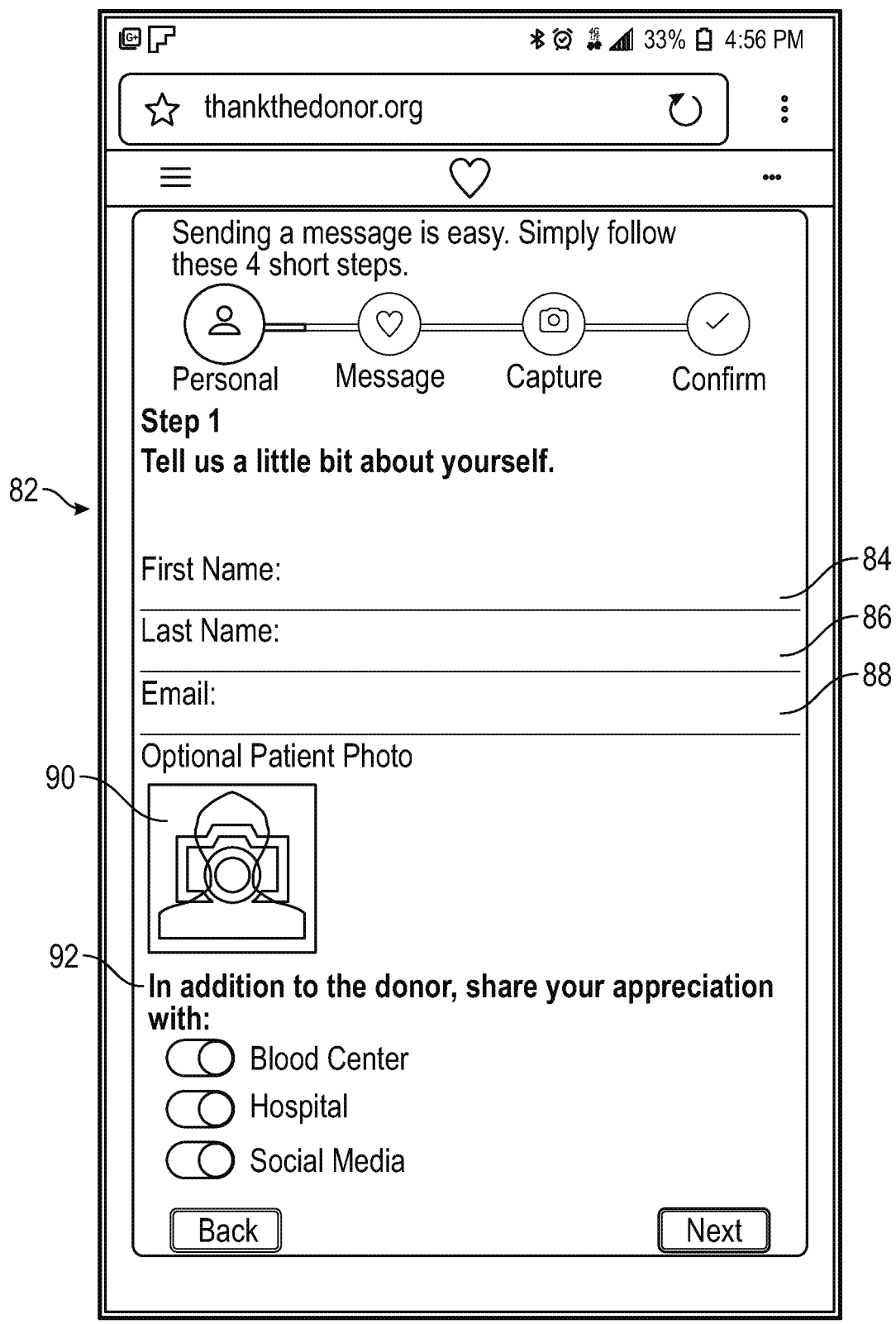

Referring to FIGS. 3 and 5, in a step 54, the receiver 14 may be directed to enter receiver data information and have fields including, but not limited to, first name 84, last name 86, e-mail 88, and/or the like, as illustrated in a screen shot 82. Other information may be collected related to the receiver 14 such as medical data, personal information, contact information, and/or the like. Additionally, in some embodiments, the receiver 14 may be prompted to upload one or more images of the receiver 14 or other relevant images associated with the receiver 14.

In a step 56, the receiver 14 may be prompted to select sharing preferences related to messaging (e.g., appreciation) as illustrated in the screen shot 82. For example, the receiver 14 may select sharing preferences for the provider 16, the intermediary 20, affiliates to the intermediary 20, social media, and/or the like.

Figure 6:
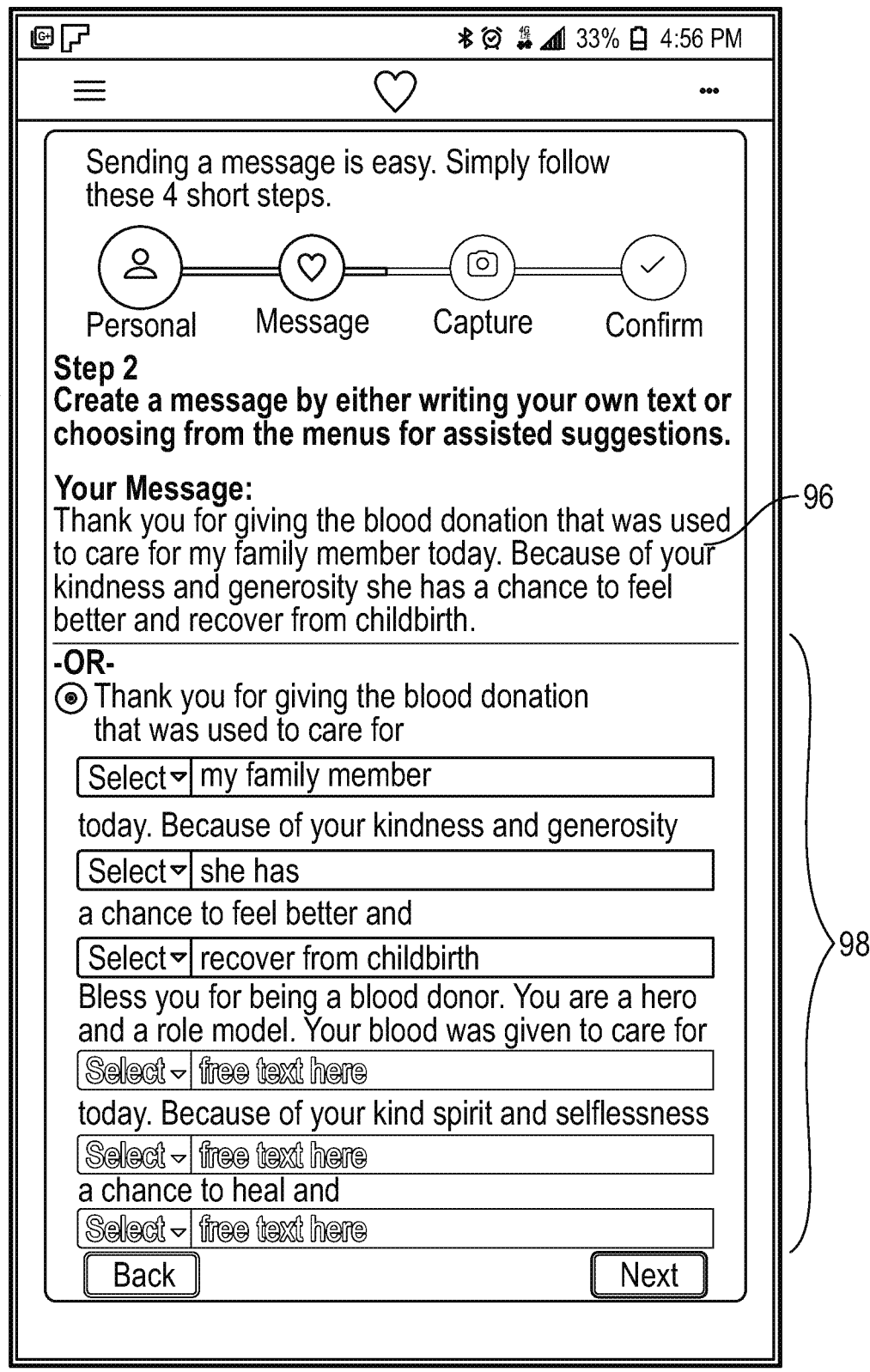
Figure 7:
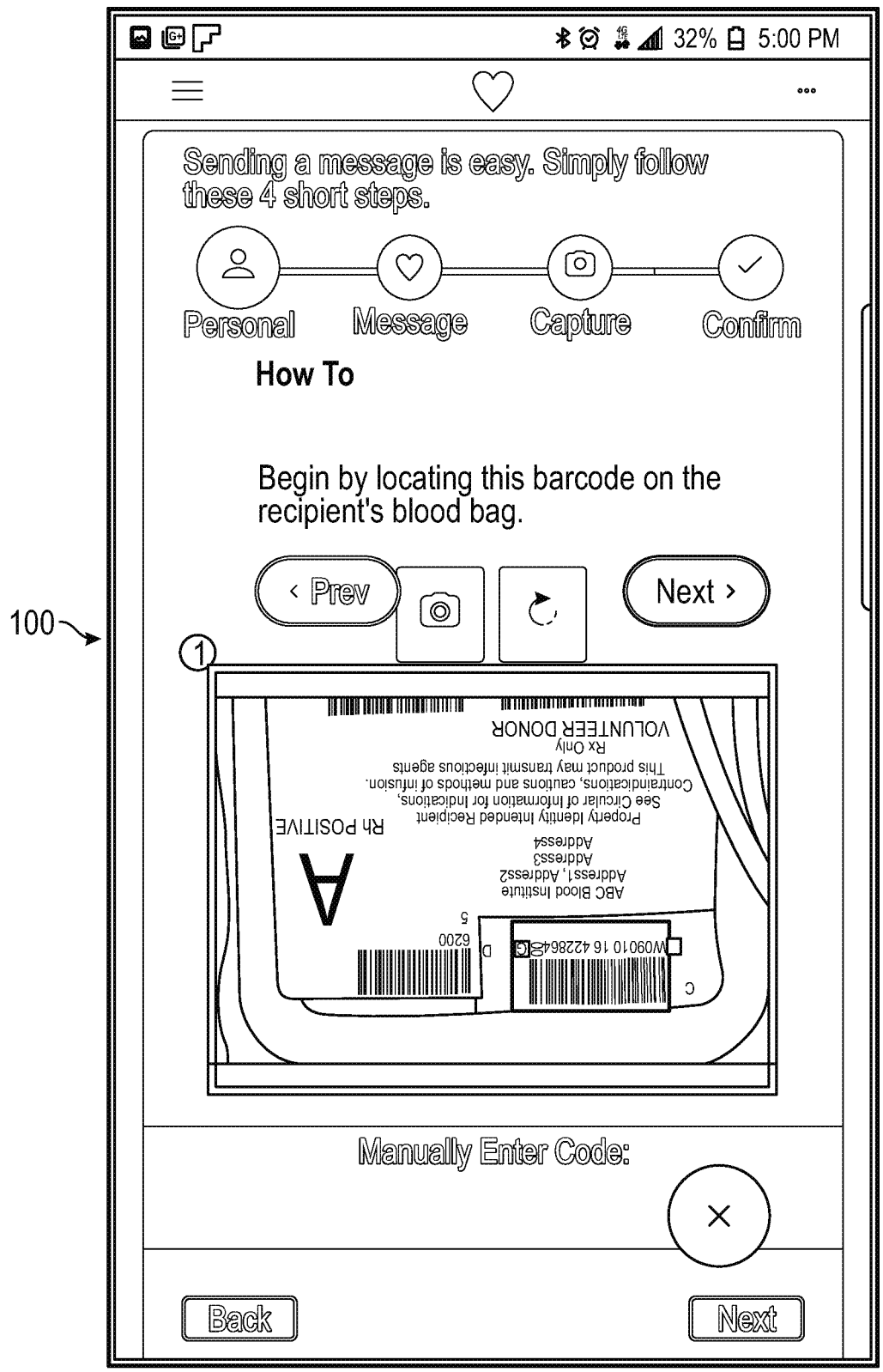

Referring to FIGS. 3 and 6, in a step 58, the receiver 14 may enter the one or more communications 12. The receiver 14 may select from predefined messages, as indicated in step 60, or may create messages, as indicated in step 62. As illustrated in the screen shot 94 of FIG. 6, the receiver 14 may be prompted to create a message by either entering text into a message field 96 or selecting a portion 98 of the screen having one or more check boxes, option buttons, and/or toggle buttons. For example, the receiver 14 may select a predefined message stating "Thank you for giving the blood donation that was used to care for my family member today" (selection underlined).

Referring to FIGS. 3 and 7-13, in steps 64-68, the receiver 14 may be prompted to provide the identifier 26 to the communication system 10. In some embodiments, the receiver 14 may have the option of providing one or more images of the identifier 26, as in step 66. Alternatively, the receiver 14 may manually enter the identifier 26, as in step 68.

Figure 8:
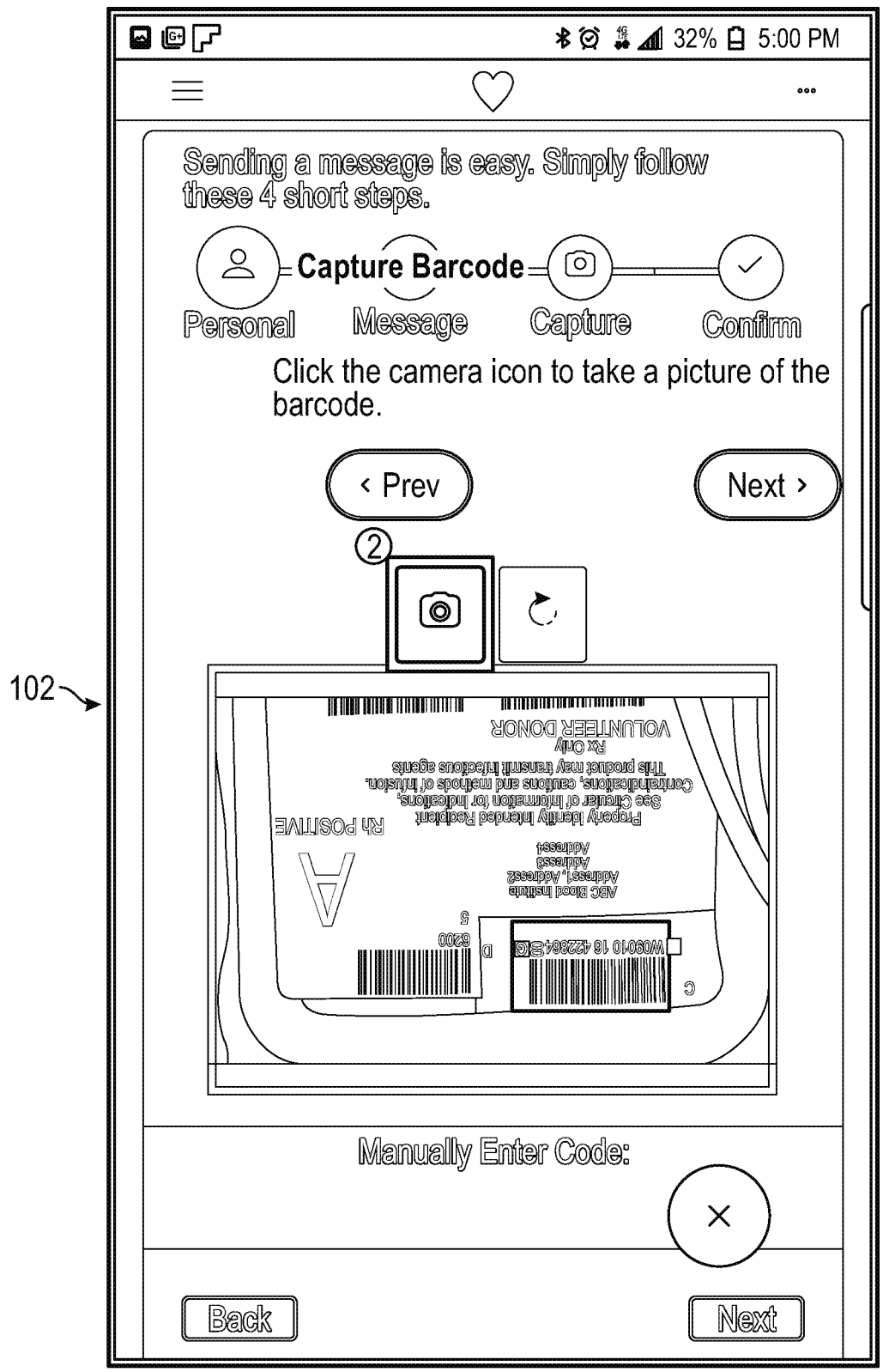
Figure 9:
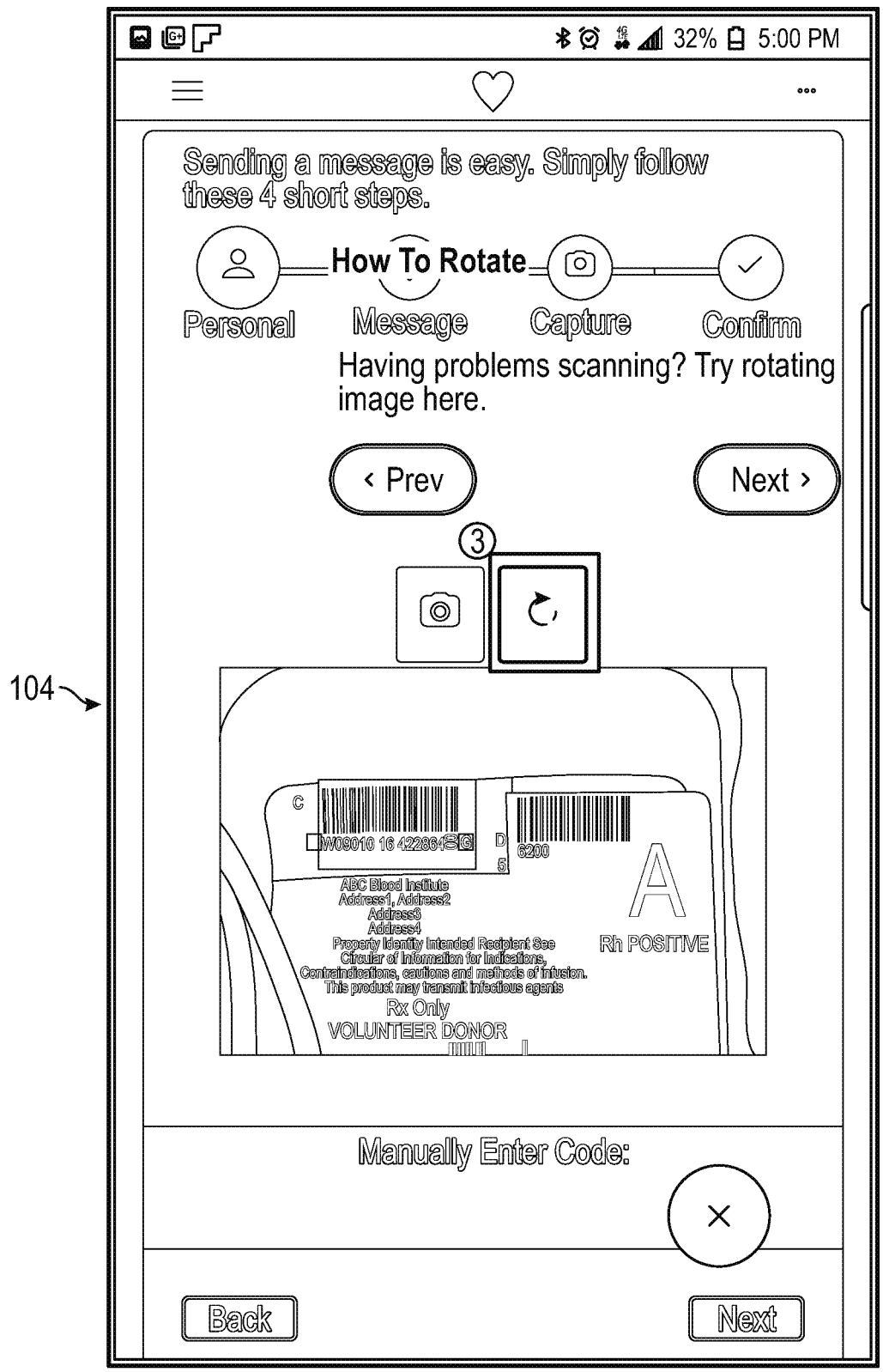
Figure 10:
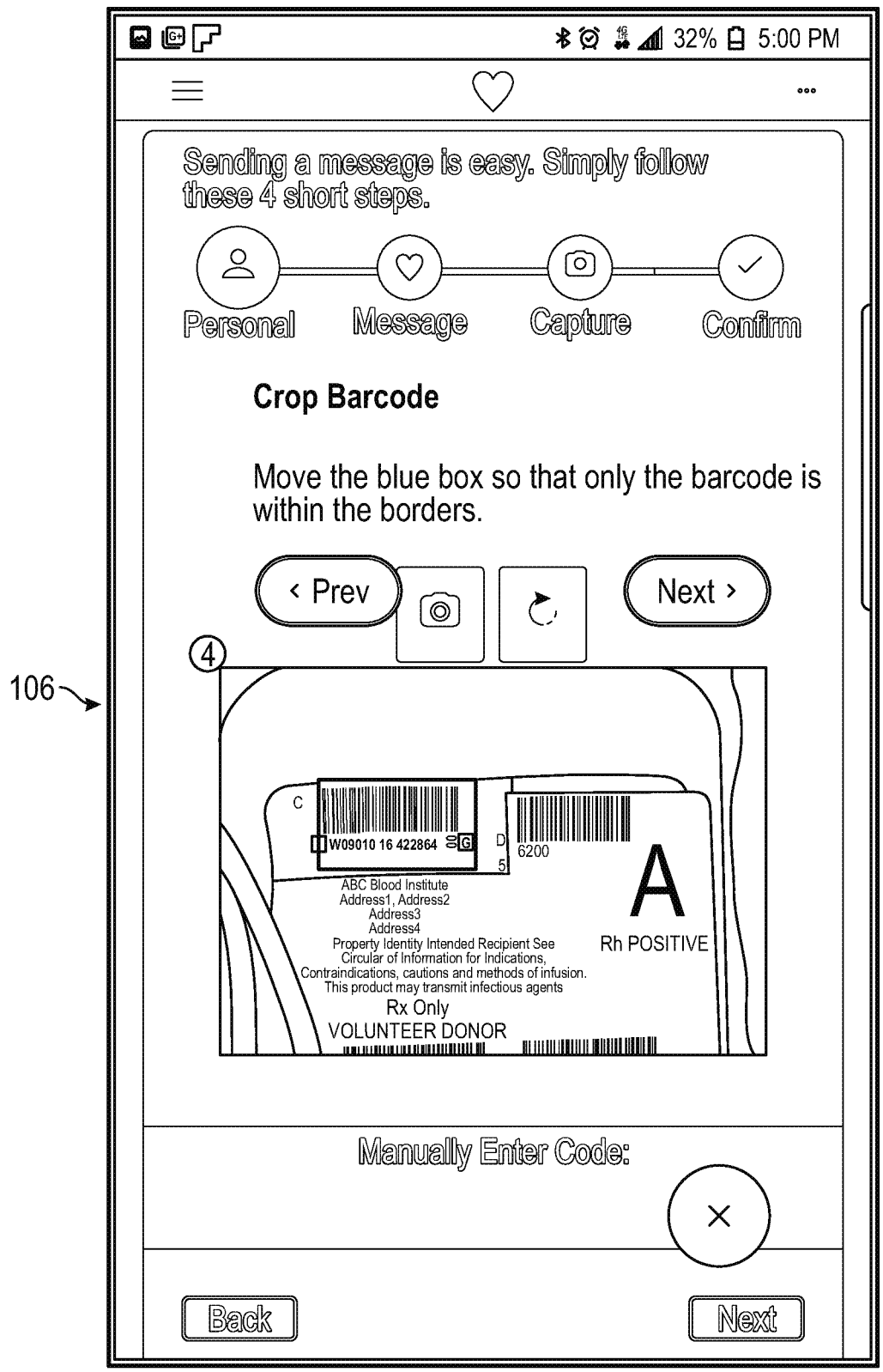
Figure 11:
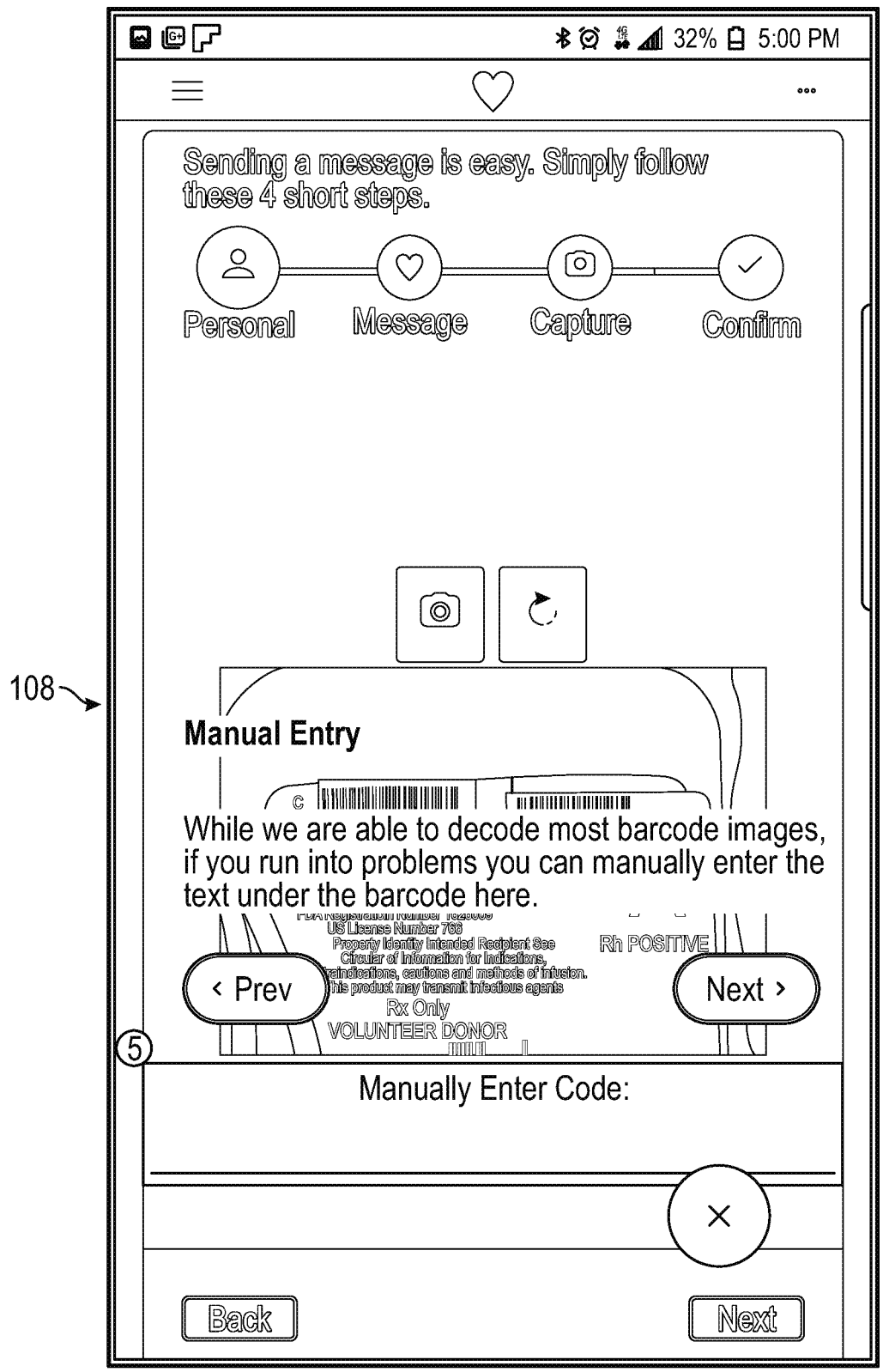
Figure 12:
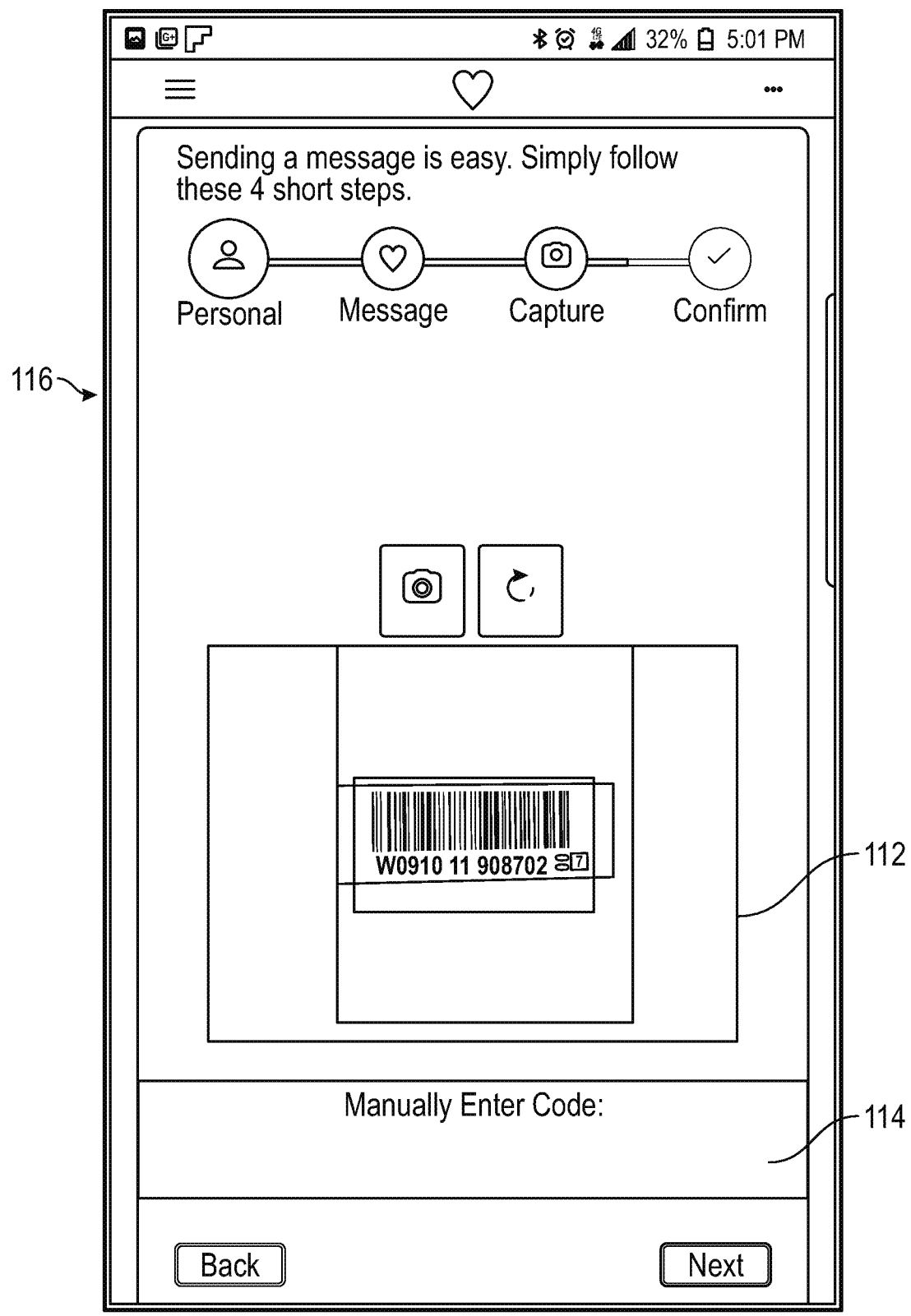

FIGS. 7-11 illustrate screenshots 100-108 of a tutorial for the receiver 14. The tutorial provides information on how to provide the identifier 26 to the communication system 10 for decoding. Generally, the receiver 14 may be prompted to locate the identifier 26 (e.g., barcode) on the product 18 as shown in screen shot 100. In screenshot 102, the receiver 14 may be prompted to click a camera icon to take an image of the identifier 26 as shown in FIG. 8. In screenshot 104, shown in FIG. 9, the receiver 14 may be prompted to rotate the captured image if there are scanning issues. In screenshot 106, shown in FIG. 10, the receiver 14 may be prompted to crop the image of the identifier 26 using a cropping box such that the identifier 26 is within borders of the cropping box. In screenshot 108, shown in FIG. 11, the receiver 14 may be informed that image capture of the identifier 26 may be unavailable, and as such, the receiver 14 may need to manually enter the identifier 26 into a field. FIG. 12 illustrates a screenshot 110 wherein the receiver may provide the identifier 26 via image 112 or manually entry via an alphanumeric field 114.

Figure 13:
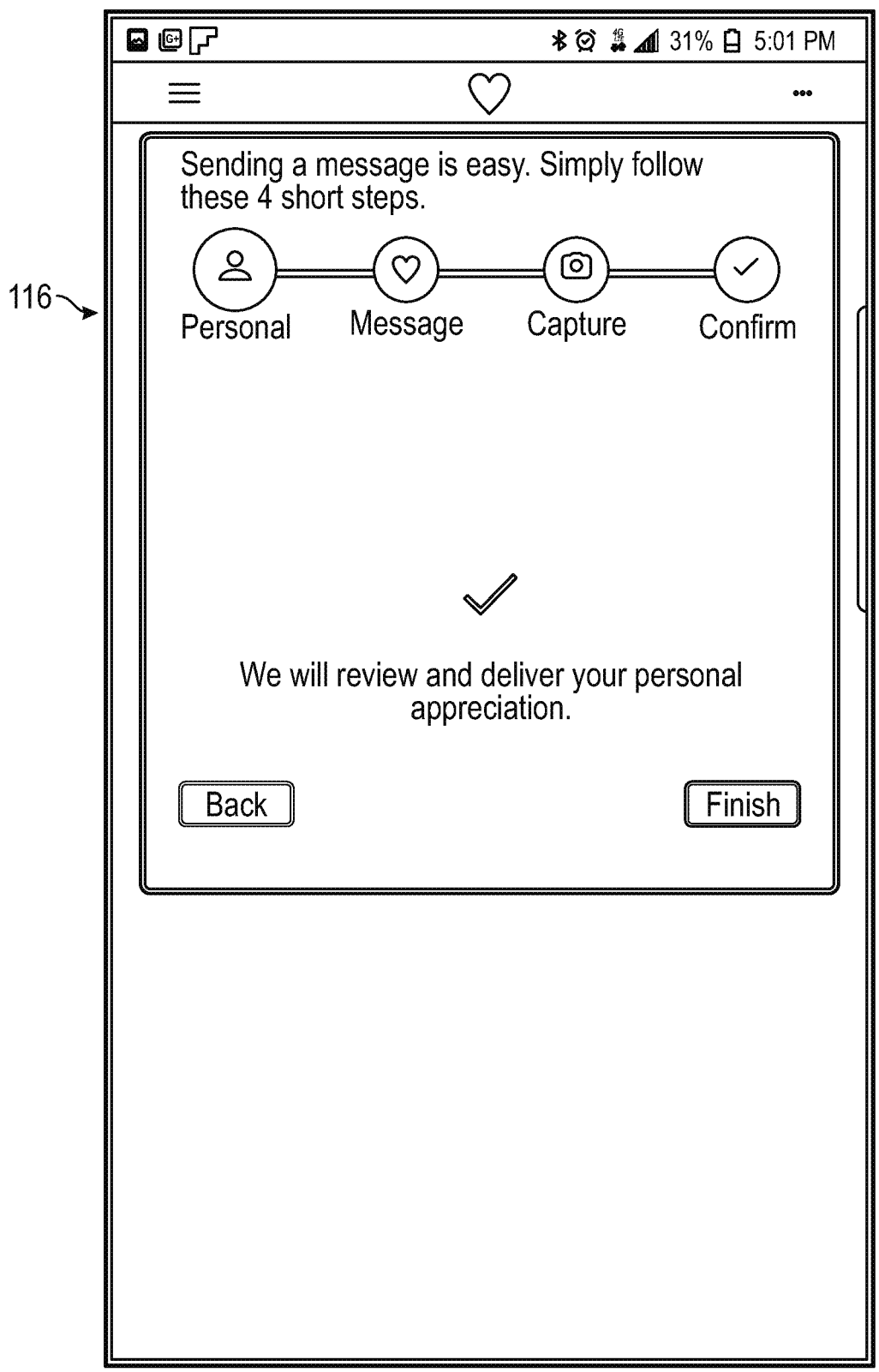

Referring to FIGS. 3 and 13, in a screenshot 116, the receiver 14 may be informed that the one or more communications will be reviewed, as illustrated in step 70, and submitted to the provider 16, as illustrated in step 72.

Figure 14:
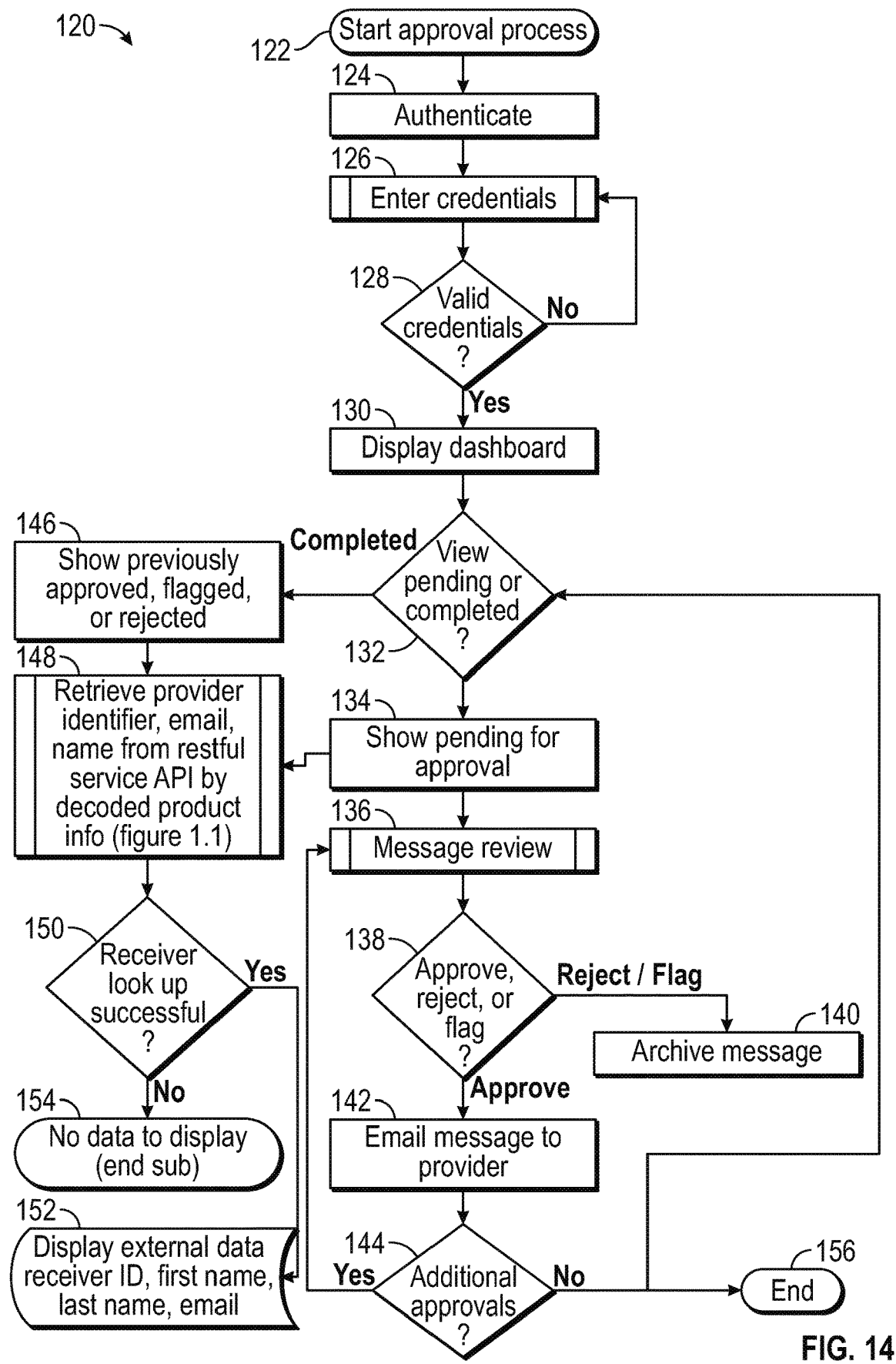
FIG. 14 illustrates a flow chart of an exemplary administrator review process for one or more communications.
Figure 15:
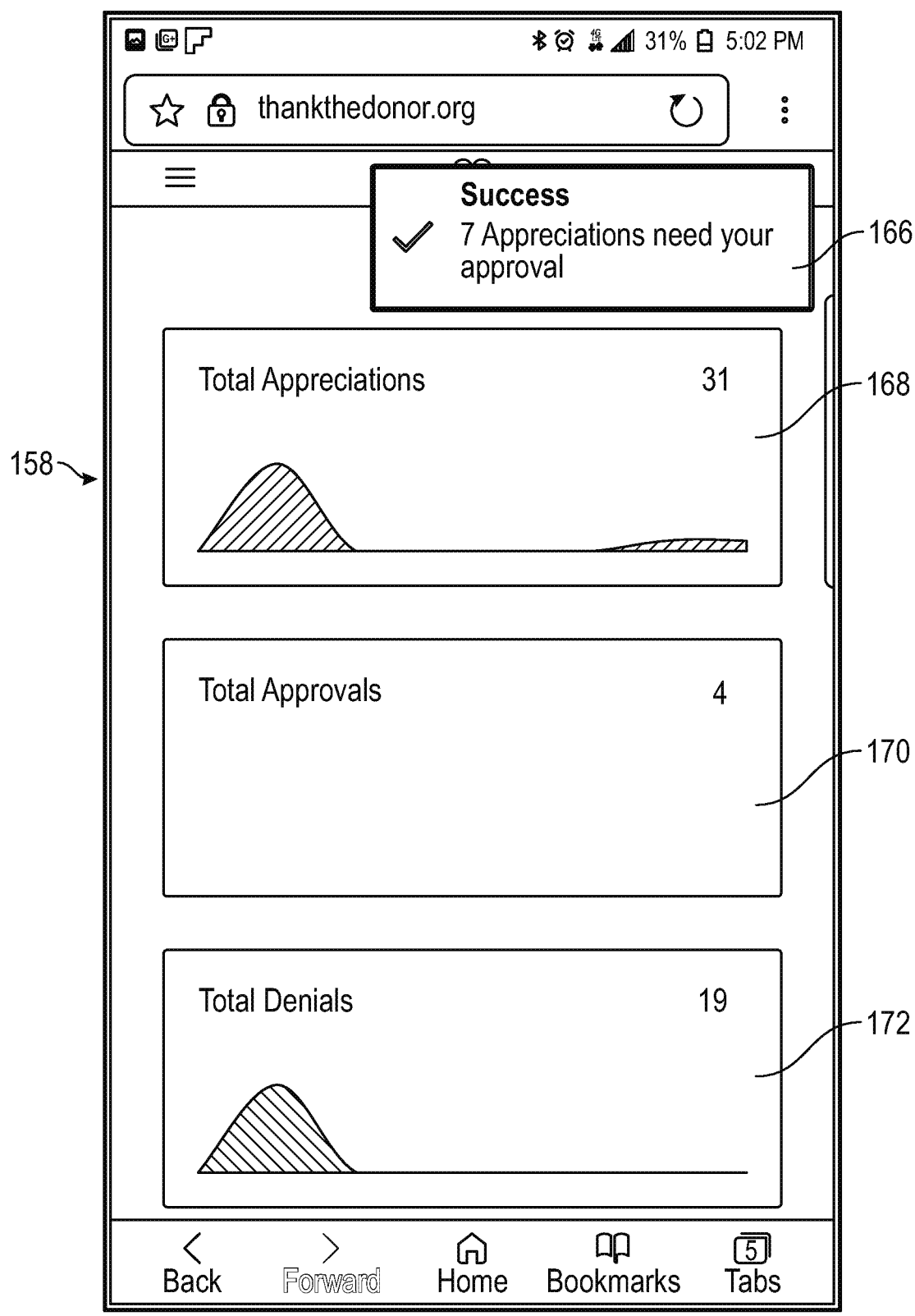
FIGS. 15-18 illustrate exemplary screenshots of the exemplary administrator review process shown in FIG. 14.
Figure 16:
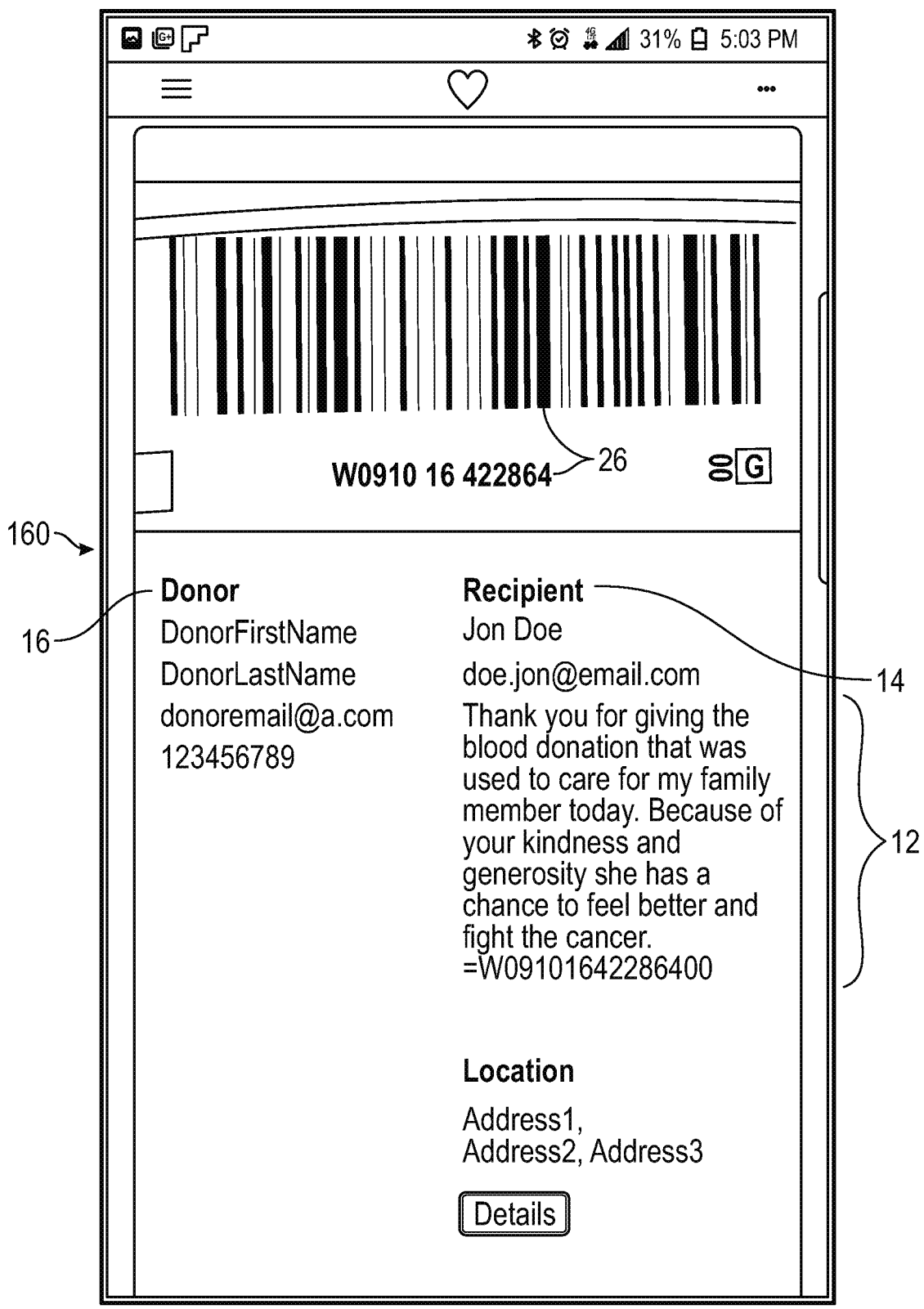

FIG. 14 illustrates a flow chart 120 of an exemplary administrator review process for the one or more communications 12. FIGS. 15-18 illustrate exemplary screenshots 158-164 for the administrator review process shown in FIG. 14.

Referring to FIG. 14, in a step 122, the administrator review process may begin by the administrator 24, shown in FIG. 1, communicating with the communication system 10. In a step 124, the administrator 24 may be authenticated by entering one or more credentials, as shown in step 126. If the credentials are validated, as shown in step 128, the administrator 24 may be directed to a display dashboard. An exemplary display dashboard is shown in the screenshot 158 of FIG. 15. The display dashboard illustrates, for example, a text message 166 indicating a number of appreciations (i.e., communications 12) needing review, a graphical representation 168 of a total number of communications 12 received, a graphical representation 170 of a total number of communications 12 approved, a graphical representation 172 of a total number of communications 12 denied, and/or the like.

Referring to FIG. 14, in a step 132, the administrator 24 may have the option of viewing pending communications 12 for review or past-reviewed (i.e., completed) communications 12. In a step 134, the administrator 24 may select to show pending communications 12 for review. In some embodiments, the communications system 10 may retrieve contact information of the provider 16 from the intermediary system 32, as shown in step 148. In some embodiments, the communications system 10 may communicate the identifier 26 to the intermediary system 32 and indicate that the intermediary system 32 may release contact information of the provider 16 to the administrator 24. If the contact information of the provider 16 is successfully acquired, as indicated in step 150, the administrator may be able to view the one or more communications 12 including information of the provider 16 and the receiver 14 as shown in a screenshot 160 in FIG. 16. In addition, the identifier 26 may be shown to the administrator 24. If the contact information of the provider 16 is not acquired, information of the receiver 14 may be shown, or the administrator 24 may view a message indicating "No Data to Display" as shown in step 154 of FIG. 3.

Figure 17:
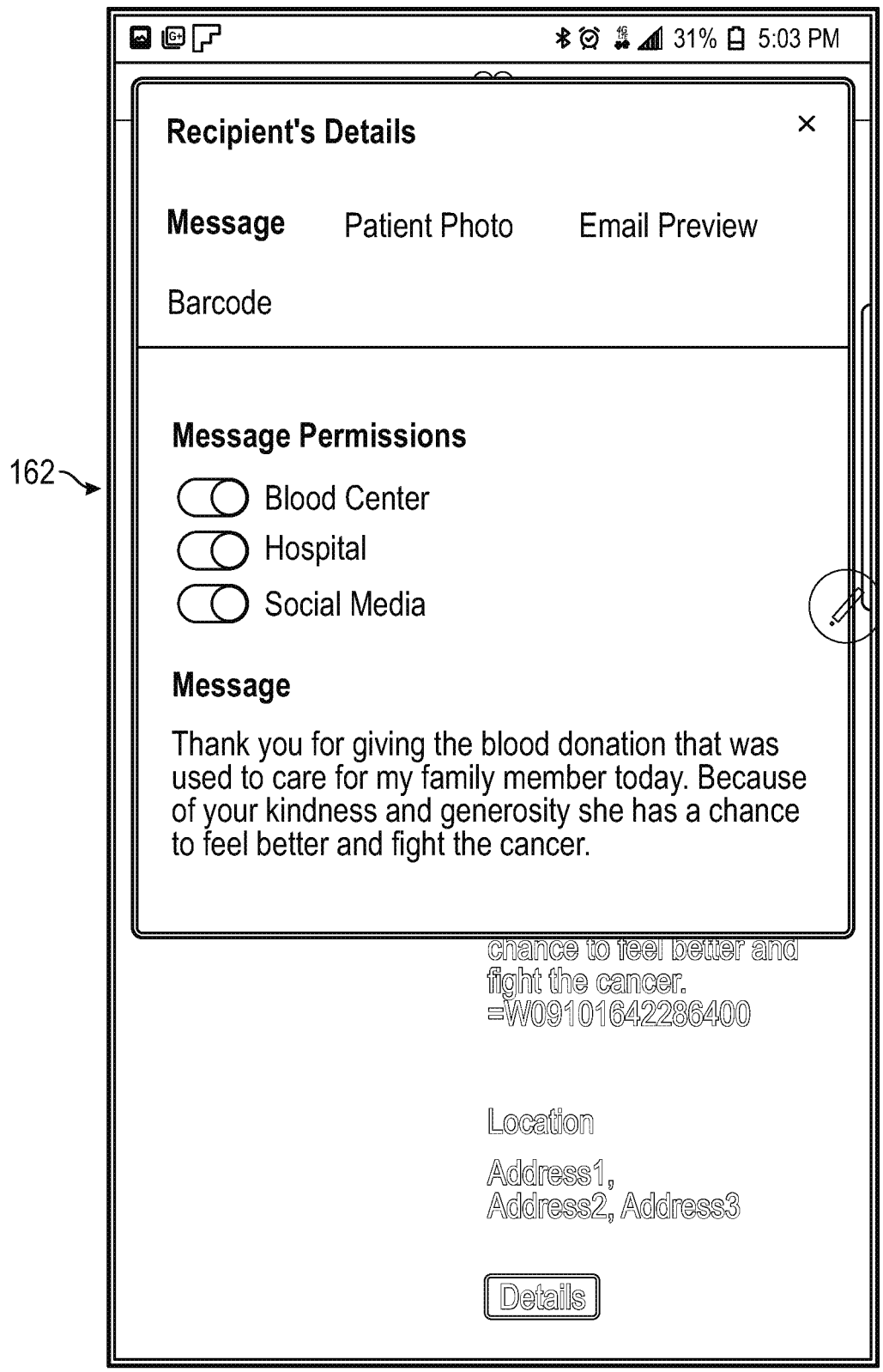
Figure 18:
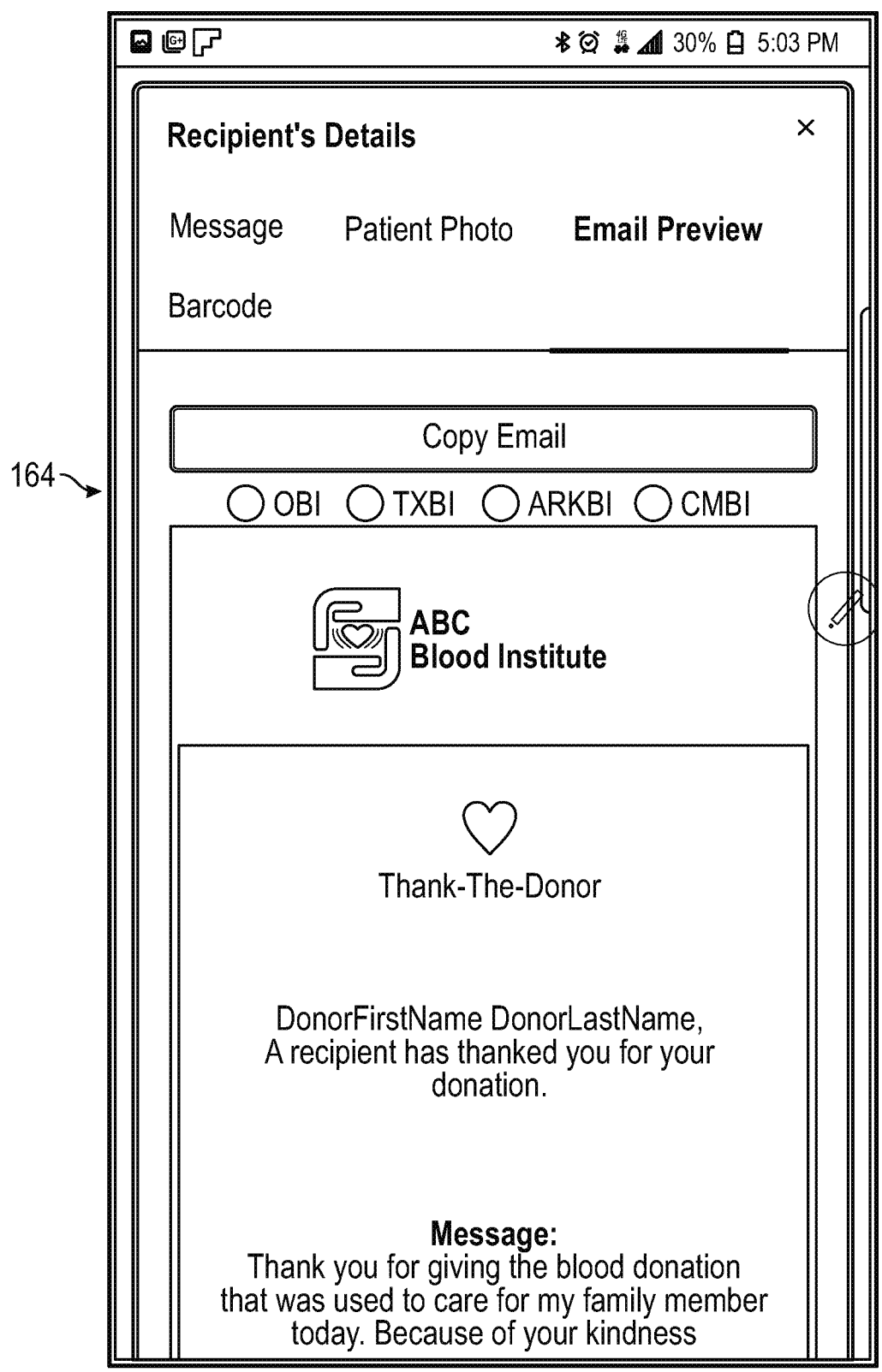

Steps 136-144 of FIG. 14 illustrate an exemplary message review process shown in screenshots 162 and 164 of FIGS. 17 and 18 respectively. In steps 136 and 138, the administrator 24 may review the one or more communications 12 and approve, reject or flag each communication. Communications 12 may be rejected for use of inappropriate language or topics, for example. If the one or more communications 12 is rejected or flagged, the communications 12 may be archived as illustrated in step 140. If the one or more communications 12 is approved, the communication 12 may be transmitted to the provider 16. Such communications 12 may be transmitted to the provider 16 via e-mail message, text message, phone message, postal service, video recording, audio recording, and/or the like.

In a step 144, the communication system 10 may identify whether there are additional communications 12 to review. If there are additional communications 12 to review, the communication system 10 may direct the administrator 24 to view pending or completed communications 12 as in step 132. Additionally, the administrator may have the option to review previously approved, flagged, and/or rejected communications 12 as indicated by step 146. If there are no further communications 12 to review, the communication system 10 may end the process as indicated by step 156.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

What is claimed is:

1. One or more non-transitory computer readable medium storing a set of computer executable instructions for running on one or more processors of a communication system that when executed by the one or more processors cause the communication system to establish communication from a receiver to an anonymous donor by:
    receiving at least one communication and an identifier from a receiver system, the receiver system being associated with the receiver who received an accommodation from a third party that was donated to the third party from the donor, the third party associated with at least one intermediary system different from both the receiver system and the communication system, the donor having an identity and contact information that is unknown by the receiver and the receiver system and that is known to the third-party and the at least one intermediary system, the identifier configured to provide identifying characteristics of the accommodation from the donor, is individualized to the accommodation from the donor, and is operable to provide, at least in part, identifying characteristics of the at least one intermediary system, the identifier not providing direct contact information of the donor;
    analyzing the identifier to determine the at least one intermediary system related to the accommodation, the intermediary system having the contact information of the donor;
    receiving the contact information of the donor from the intermediary system, wherein the contact information of the donor is not disclosed to the receiver, whereby an identity of the donor, and contact information of the donor remains confidential to the receiver; and
    transmitting the at least one communication to the donor of the accommodation using the contact information from the intermediary system.

2. The one or more non-transitory computer readable medium storing the set of computer executable instructions for running on one or more processors of claim 1, further comprising reviewing the at least one communication prior to transmission to the donor.

3. The one or more non-transitory computer readable medium storing the set of computer executable instructions for running on one or more processors of claim 2, wherein review of the at least one communication includes accessing, by an administrator, the one or more processors to view the at least one communication.

4. The one or more non-transitory computer readable medium storing the set of computer executable instructions for running on one or more processors of claim 1, wherein the donor is a blood donor and the accommodation is blood product.

5. The one or more non-transitory computer readable medium storing the set of computer executable instructions for running on one or more processors of claim 1, wherein the identifier is received in an image.

6. The one or more non-transitory computer readable medium storing the set of computer executable instructions for running on one or more processors of claim 1, wherein the identifier is received as a code.

7. The one or more non-transitory computer readable medium storing the set of computer executable instructions for running on one or more processors of claim 1, wherein the identifier is an alphanumeric code.

8. The one or more non-transitory computer readable medium storing the set of computer executable instructions for running on one or more processors of claim 1, wherein the identifier is an ISBT 128 donation identification number.

9. The one or more non-transitory computer readable medium storing the set of computer executable instructions for running on one or more processors of claim 1, wherein the intermediary is the third party.

10. An automated method performed by a communication system having at least one processor running computer executable instructions stored on at least one non-transitory computer readable medium, comprising:
    receive at least one communication intended for a donor of a donated accommodation, wherein the donor donated the donated accommodation to a third party associated with an intermediary system, and an identifier of the donated accommodation from a receiver of the donated accommodation, the receiver having received the donated accommodation from the third party, the identifier providing, at least in part, identifying characteristics of the intermediary system and being individualized to the donated accommodation, the identifier not providing direct contact information of the donor;
    analyze the identifier to determine the intermediary system having the contact information for the donor;
    receive the contact information of the donor; and,
    transmit the at least one communication to the donor using the contact information received;
wherein the contact information of the donor is not disclosed to the receiver, whereby an identity of the donor, and contact information of the donor remains confidential to the receiver, and wherein the intermediary system is different from both the receiver system and the communication system.

11. The automated method of claim 10, further comprising the step of reviewing, by an administrator, the at least one communication prior to transmission to the donor.

12. The automated method of claim 11, wherein each communication is classified as approved, rejected or flagged.

13. The automated method of claim 12, wherein rejected and flagged communications are archived in at least one database.

14. The automated method of claim 10, wherein the donor is a blood donor and the accommodation is a blood product.

15. The automated method of claim 10, wherein the identifier is an image of a barcode.

16. The automated method of claim 10, wherein the identifier is a numeric code.

* * * * *